United States Patent [19]
Laitinen

[11] Patent Number: 5,973,206
[45] Date of Patent: Oct. 26, 1999

[54] HYDROGENATION OF AROMATIC NITROCOMPOUNDS TO AROMATIC AMINES

[75] Inventor: Antero Laitinen, Helsinki, Finland

[73] Assignee: Valtion Teknillinen Tutkimuskeskus, Espoo, Finland

[21] Appl. No.: 09/125,422

[22] PCT Filed: Feb. 18, 1997

[86] PCT No.: PCT/FI97/00099

§ 371 Date: Oct. 19, 1998

§ 102(e) Date: Oct. 19, 1998

[87] PCT Pub. No.: WO97/30967

PCT Pub. Date: Aug. 28, 1997

[30] Foreign Application Priority Data

Feb. 23, 1996 [FI] Finland ..................................... 960818

[51] Int. Cl.[6] .................................................. C07C 209/00
[52] U.S. Cl. ............................................................ 564/423
[58] Field of Search ............................................. 564/423

[56] References Cited

U.S. PATENT DOCUMENTS

| | | |
|---|---|---|
| 2,891,094 | 6/1959 | Karkalits, Jr. . |
| 3,265,636 | 8/1966 | Speigler ................................. 252/447 |
| 5,241,048 | 8/1993 | Barstow et al. ......................... 530/334 |

FOREIGN PATENT DOCUMENTS

| | | |
|---|---|---|
| 629442A1 | 8/1994 | European Pat. Off. . |
| 9601304 | 1/1996 | European Pat. Off. . |
| 8908659 | 9/1989 | WIPO . |

OTHER PUBLICATIONS symposium series (1996), 626 (Green chemistry), 208. National Meeting of the American Chemical Society, Aug. 21–25, 1994, Paul T. Anastas, editor et al. "Supercritical Carbon Dioxide as a Substitute Solvent for Chemical Sythesis and Catalysis", pp. 132–151.

Jett C. Arthur, Jr., "Physical Organic Chemistry", vol. 121, 1994 p. 942, and vol. 109, 1988 p. 739.

Agric. Biol. Chem., 51 (12), 1987, Masamichi Kamihira, et al. Synthesis of Aspartame Precursors by Enzymatic Reaction in Supercritical Carbon Dioxide, pp. 3427–3428.

*Primary Examiner*—Samuel Barts

[57] ABSTRACT

A method for the hydrogenation of aromatic nitrocompounds to aromatic amines, which comprises mixing an aromatic nitrocompound, hydrogen gas and a solvent together under elevated pressure and temperature to form a homogenous mixture in a supercritical or near-critical state and bringing the resulting homogenous mixture into contact with a catalyst to form the aromatic amine product.

7 Claims, No Drawings

HYDROGENATION OF AROMATIC NITROCOMPOUNDS TO AROMATIC AMINES

This application is the national phase under 35 U.S.C. §371 of prior PCT International Application No. PCT/FI97/00099 which has an International filing date of Feb. 18, 1997 which designated the United States of America, the entire contents of which are hereby incorporated by reference.

TECHNICAL TECHNICAL FIELD OF THE INVENTION

The present invention concerns a method for the hydrogenation of aromatic nitrocompounds to aromatic amines.

BACKGROUND OF THE INVENTION

Aromatic nitrocompounds are compounds where one or more nitro-groups are bound to a carbon atom in an aromatic ring. Typical aromatic nitrocompounds are e.g. nitrobenzene, nitrotoluene, nitroxylene and dinitrotoluene. Aromatic nitrocompounds can be hydrogenated to correspnding aromatic amines.

It is well known that many of the relatively high boiling aromatic amines can be prepared by liquid-phase hydrogenation of the corresponding aromatic nitrocompound in the presence of a catalyst, either with or without the use of a solvent[1]. Early catalytic hydrogenations were performed in stirred batch reactors. In this known method the aromatic nitrocompound is first dissolved into a suitable solvent and pumped into a batch reactor containing the catalyst. The reactor which is equipped with a stirrer is pressurized by hydrogen gas. After the reaction is completed, the product can be separated from the solvent.

More recently batch processes have been replaced by continuous processes. A continuous liquid-phase process is illustrated by the process for diaminotoluene[2,3]. According to the process, dinitrotoluene (DNT) is catalytically hydrogenated at 150–200 bar and about 100° C. A solution, which contains about 25 wt-% dinitrotoluene dissolved in methanol, hydrogen and Raney-nickel, is pumped through a series of reactors. Reactors are equipped with internal circulation to make the reaction more complete. After the reaction is completed, the pressure is reduced and the excess hydrogen removed in a gas-liquid separator and recycled to the beginning of the process. Catalyst is then removed and recycled, after which the solvent is distilled and recycled. The water is removed in the dehydration column. The product purity is more than 99-% pure diaminotoluene.

Low molecular weight alcohols, particularly methanol or ethanol, are the most commonly used hydrogenation solvents for hydrogenation of aromatic nitrocompounds. Other solvents, like acetic acid, ammonia, benzene, glycerol ethylene glycol, hydrochloric acid, sulfuric acid or water can be used.

It is well known that the solubility of hydrogen into liquid-like solvents is extremely small. Due to the this low hydrogen solubility and slow transfer to the catalyst surface where the reaction product is formed, the reaction in liquid-phase is relatively slow, and continuous reactors could not always be used effectively. Several mechanical solutions have been introduced. One solution is to use a spray column where the solvent, nitroaromatic compound and catalyst are sprayed with the hydrogen gas.

It is known that aromatic nitrocompounds can be hydrogenated in the vapor phase. In this method a vaporized nitroaromatic compound and hydrogen gas flow through the catalyst bed forming the product. The reaction is usually very fast and high conversions are obtained with a single pass. This method is continuous and in principle simple. A method for producing aniline from nitrobenzene in a trickle-bed reactor is described in the literature[4]. Nitrobenzene is first vaporized and mixed with a 200% excess of hydrogen gas. The hot gaseous mixture flows upward into the reduction chamber containing the copper-silica catalyst. The reaction is very fast at 270° C. and 2–3 bar. After leaving the reactor, the reaction mixture containing aniline, hydrogen and water is cooled. Excess hydrogen is first removed after which water and aniline are separated. Finally aniline is purified to a 99% product.

The catalytic hydrogenation of aromatic nitrocompounds to aromatic amines can be done in the vapor phase, provided that he boiling point of the compound is low enough and the starting material and the product are thermally stabile. These limitations mean that only relatively simple aliphatic and aromatic nitrocompounds, such as nitrobenzene and nitroxylene, can be hydrogenated in the vapor phase.

SUMMARY OF THE INVENTION

The present invention is based upon the discovery that aromatic nitrocompounds can be hydrogenated in the presence of a hydrogenating catalyst in a solvent, which is in the supercritical or near-critical state. The aromatic nitrocompound and hydrogen gas are dissolved into the supercritical or near-critical state solvent. The resulting homogenous mixture which is in the supercritical or near-critical state is brought into contact with the catalyst, and the reaction product, i,e., the aromatic amine, is formed. The hydrogen concentration of the homogenous mixture can be chosen freely and thus is not a restricting factor in the reaction. With the assistance of the present invention a decisive improvement on previously mentioned process limitations in the prior art can be obtained.

The word supercritical refers to the state of the solvent. For example carbon dioxide is in a supercritical state when its temperature is above 31.1° C. and simultaneously the pressure is above 73.8 bar. Corresponding values for ethane are 32.4° C. and 48 bar, and for propane 96.8° C. and 42 bar. Supercritical fluids exhibit both liquid- and gas-like properties, such as liquid-like density and gas-like viscosity. The diffusivity of supercritical fluids is between the values of gases and liquids. Gas-like properties are considered to be beneficial in reaction chemistry due to enhanced mass transfer.

A particularly important property of supercritical fluids is, that they are almost completely miscible with all kind of gases, including hydrogen gas. This means that when the solvent is in a supercritical state the hydrogen gas needed to reduce the aromatic nitrocompound to aromatic amines can be easily mixed with the solvent. In the reactors where the reaction is carried out in a vapor phase, the nitroaromatic compound is vaporized and mixed with hydrogen gas, which efficiently removes the mass transfer limitations encountered in liquid phase systems.

However, relatively high temperatures, i.e. 300–475° C., are often needed in the vapor phase systems. According to the present invention complete miscibility of the nitroaromatic compound and hydrogen is obtained at significantly lower temperatures, i.e. 30–150° C.

The present invention makes possible the construction of more simple and more efficient reactors for nitroaromatic amine production. Applying the supercritical solvent can also simplify the overall process, for example the separation and purification of the product. The supercritical solvent, being usually a pressurized gas, can be relatively easily separated from the product by simply depressurising the solvent mixture. The reaction can be carried out in batch reactors, but obviously continuous reactor systems are preferable in industrial practice.

Carbon dioxide, which is environmentally acceptable, non-toxic, non-flammable, relatively inexpensive, non-corrosive and easily available can be utilized in the present invention. Carbon dioxide is used in fire fighting to extinguish the flames. Carbon dioxide can act both as a solvent and as a safe gas in the hydrogenation processes. Low molecular weight hydrocarbons can also be used, such as, for example, ethane and propane, which are chemically stable against hydrogenation, which means that higher hydrogenation temperatures than in the case of carbon dioxide are required.

It is well known that the character of supercritical solvent can be enhanced by addition of a modifier like short chain alcohols or esters.

DETAILED DESCRIPTION OF THE INVENTION

The present invention is described in detail in connection with the following examples which are given as exemplary and not limitative of the present invention.

EXAMPLE 1

Reduction of methyl-p-nitrobenzoate in Carbon Dioxide with Pd-Containing Catalyst 0.5 g methyl-p-nitrobenzoate (mp. 94–96° C.) and 0.057 g catalyst were weighted and placed into the batch reactor (40 mL), after which the reactor was closed. The catalyst used was palladium on polyolefinfiber. The batch reactor was purged with carbon dioxide to remove the entrapped air, and was heated to 42° C. The system was then charged with carbon dioxide and hydrogen gases, so that the total pressure was 180 bar and hydrogen partial pressure was 15 bar. The pressurized reaction mixture was magnetically mixed for 30 minutes, after which the mixer was turned off and the reaction vessel was rapidly cooled and depressurized. The catalyst was then separated from the product. The product was analyzed with Thin Layer Chromatography (TLC) and with liquid chromatography, and was noted to be almost pure methyl-p-aminobenzoate. The purity was over 95%.

EXAMPLE 2

Reduction of methyl-p-nitrobenzoate in Carbon Dioxide with Ni-Containing Catalyst Using procedures similar to example 1., methyl-p-nitrobenzoate was hydrogenated. The catalyst was nickel on carbon and the reaction temperature was 100° C. The total pressure was 80 bar and the hydrogen partial pressure was 10 bar. The product was analyzed and purity of methyl-p-aminobenzoate was over 70%.

EXAMPLE 3

Reduction of methyl-p-nitrobenzoate in Carbon Dioxide with Pt-Containing Catalyst Using procedures similar to example 1., methyl-p-nitrobenzoate was hydrogenated. The catalyst was platinum on activated carbon and the reaction temperature was 35° C. A small amount of methanol was used as a modifier. The total pressure was 250 bar and the hydrogen partial pressure was 40 bar. The product was analyzed and purity of methyl-p-aminobenzoate was over 90%.

EXAMPLE 4

Reduction of methyl-p-nitrobenzoate in Carbon Dioxide with CuO/CrO-Containing Catalyst Using procedures similar to example 1., methyl-p-nitrobenzoate was hydrogenated. The catalyst contained copperoxide/chromiumoxide. The reaction temperate was 150° C., total pressure was 300 bar and the hydrogen partial pressure was 20 bar. The product was analyzed and purity of methyl-p-aminobenzoate was over 60%.

EXAMPLE 5

Reduction of nitrobenzene in Carbon Dioxide with Pd-Containing Catalyst 0.5 g nitrobenzene (mp. 5–7° C.) and 0.051 g catalyst were weighted and placed into the batch reactor (40 mL), after which the reactor was closed. The catalyst used was palladium on polyolefinfiber. The batch reactor was purged with carbon dioxide to remove the entrapped air, and was heated to 40° C. The system was then charged with carbon dioxide and hydrogen gases, so that the total pressure was 200 bar and hydrogen partial pressure was 20 bar. Pressurized reaction mixture was magnetically mixed for 30 minutes, after which the mixer was turned off and the reaction vessel was rapidly cooled and depressurized. The catalyst was then separated from the product. The product was analyzed with Thin Layer Chromatography (TLC) and with liquid chromatography, and was noted to be over 90% pure aniline.

EXAMPLE 6

Reduction of 2,4-dinitrotoluene in Carbon Dioxide with Pd-Containing Catalyst 0.5 g 2,4-dinitrotoluene (mp. 67–70° C.) and 0.27 g catalyst were weighted and placed into the batch reactor (40 mL), after which the reactor was closed. The catalyst used was palladium on polyolefinfiber. The batch reactor was purged with carbon dioxide to remove the entrapped air, and was heated to 42° C. The system was then charged with carbon dioxide and hydrogen gases, so that the total pressure was 200 bar and hydrogen partial pressure was 19 bar. Pressurized reaction mixture was magnetically mixed for 30 minutes, after which the mixer was turned off and the reaction vessel was rapidly cooled and depressurized. The catalyst was then separated from the product. The product was analyzed with Thin Layer Chromatography (TLC) and with liquid chromatography, and was noted to be over 90% pure 2,4-diaminotoluene.

EXAMPLE 7

Reduction of 2,4-dinitrotoluene in Carbon Dioxide with Ni-Containing Catalyst

Using procedures similar to example 1., methyl-p-nitrobenzoate was hydrogenated. The catalyst contained nickel on activated carbon. The temperature was 80° C. Total pressure was 250 bar and hydrogen partial pressure was 30 bar. The product was analyzed with Thin Layer Chromatography (TLC) and with liquid chromatography, and was noted to be over 85% pure 2,4-diaminotoluene.

EXAMPLE 8

Reduction of methyl-p-nitrobenzoate in Propane with Pd-Containing Catalyst 0.5 g methyl-p-nitrobenzoate and 0.2 g catalyst are weighted and placed into a batch reactor (40 mL), after which the reactor is closed. The catalyst is palladium on carbon. The batch reactor is purged with propane to remove the entrapped air, and is heated to 105° C. The system is then charged with propane and hydrogen gases, so that the total pressure is 75 bar and hydrogen partial pressure is 20 bar. Pressurized reaction mixture is magnetically mixed for 30 minutes, after which the mixer is turned off and the reaction vessel is rapidly cooled and depressurized. The catalyst is then separated from the product. The methyl-p-aminobenzoate product is analyzed with Thin Layer Chromatography (TLC) and with liquid chromatography.

EXAMPLE 9

Reduction of methyl-p-nitrobenzoate in Ethane with Pd-Containing Catalyst 0.5 g methyl-p-nitrobenzoate and 0.2 g catalyst are weighted and placed into a batch reactor (40 mL), after which the reactor is closed. The catalyst is palladium on carbon. The batch reactor is purged with ethane to remove the entrapped air, and is heated to 40° C. The system is then charged with ethane and hydrogen gases, so that the total pressure is 90 bar and hydrogen partial pressure is 20 bar. Pressurized reaction mixture is magnetically mixed for 30 minutes, after which the mixer is turned off and the reaction vessel is rapidly cooled and depressurized. The catalyst is then separated from the product. The methyl-p-aminobenzoate product is analyzed with Thin Layer Chromatography (TLC) and with liquid chromatography.

This invention has above been illustrated by referring to certain favorable examples. It has not been intended to limit the scope of this invention to the above examples. Several modifications are possible, including stating materials, products, catalyst, pressure, temperature, time or operating mode, i.e. batch or continuous.

Literature Cited

1. J. I. Kroschwitz, M. Howe-Grant, Eds.; Kirk-Othmer, Encyclopedia of Chemical Technology, $4^{th}$ ed., vol 2, page 489.
2. H. Dierichs and H. Holzrichter, U.S. Pat. No. 3,032,586 (Apr. 18, 1957)
3. H. Dierichs and H. Hoizrichter, Brit. Pat. 768 111 (Feb. 13, 1957).
4. O. C. Karkalits, Jr., C. M. Vanderwaart and F. H. Megson; U.S. Pat. No. 2,891,094 (Jun. 16, 1959)

What is claimed is:

1. A method for the hydrogenation of aromatic nitrocompounds to aromatic amines, which comprises mixing
    an aromatic nitrocompound, hydrogen gas and a solvent together under elevated pressure and temperature to form a homogenous mixture in a supercritical or near-critical state and bringing the resulting homogenous mixture into contact with a catalyst to form the aromatic amine product.
2. The method according to claim 1, wherein the solvent is selected from the group consisting of carbon dioxide, ethane, propane or a binary or ternary mixture thereof.
3. The method according to claim 1, wherein the catalyst contains palladium-, platinum-, copper-, chromium- or nickel.
4. The method according to claim 1, wherein methanol is added as a modifier.
5. The method of claim 1, wherein the aromatic nitrocompound is methyl-p-nitrobenzoate, 2,4-dinitrotoluene or nitrobenzene and the aromatic amine is methyl-p-aminobenzoate, 2,4-diaminotoluene or aniline.
6. The method of claim 1, wherein the catalyst is selected from the group consisting of palladium/carbon, palladium/polyolefin fiber, platinum/carbon, nickel/carbon and copper oxide/chromium oxide.
7. The method of claim 1, wherein the solvent is in said supercritical or near critical state.

* * * * *